US00PP10651P

United States Patent [19]

Kovacevich

[11] Patent Number: Plant 10,651

[45] Date of Patent: Oct. 20, 1998

[54] APRICOT TREE NAMED 'LOUISA'

[76] Inventor: John J. Kovacevich, 4001 Pinehurst, Bakersfield, Calif. 93306

[21] Appl. No.: 729,340

[22] Filed: Oct. 16, 1996

[51] Int. Cl.[6] ..... A01H 5/00

[52] U.S. Cl. ..... Plt./39

[58] Field of Search ..... Plt./39

[56] References Cited

U.S. PATENT DOCUMENTS

P.P. 9,173 6/1995 Howard ..... Plt./39

*Primary Examiner*—Howard J. Locker

*Attorney, Agent, or Firm*—Worrel & Worrel

[57] ABSTRACT

A new and distinct variety of apricot tree, *Prunus armeniaca*, which is somewhat remotely similar to the 'Castlebrite' apricot tree (unpatented), but from which it is distinguished by producing fruit which are mature for harvesting and shipment approximately May 15 to May 25, or about three days to five days after the fruit produced by the 'Castlebrite' apricot tree and wherein the fruit is larger with a substantially sweeter flavor, and milder texture.

1 Drawing Sheet

BACKGROUND OF THE NEW VARIETY

The present invention relates to a new and distinct variety of apricot tree, which will hereinafter be denominated varietally as the 'Louisa' apricot tree, and, more particularly, to an apricot tree which produces fruit mature for commercial harvesting and shipment May 15 to May 25, or about three days to five days after the 'Castlebrite' apricot tree (unpatented) in the San Joaquin Valley of central California.

Commercially successful, fresh market apricot varieties typically are characterized by possessing superior attributes in several of a plurality of criteria including producing fruit having high skin coloration, appealing flavor and texture, commercially viable ripening dates and shipping quality, comparatively large size and the like. The 'Castlebrite' apricot tree has been commercially successful due to a number of commercially attractive characteristics. However, the industry is always exploring for new varieties which may have superior attributes in these regards over known commercial varieties and which produce fruit having ripening dates compatible with those of such known varieties.

The apricot tree of the instant new variety was derived from the 'Castlebrite' apricot tree, but is distinguishable therefrom and believed superior thereto in that it produces fruit which ripens about three to five days after the fruit of the 'Castlebrite' apricot tree in the San Joaquin Valley of central California, which is consistently larger and which is substantially sweeter than the fruit of the 'Castlebrite' apricot tree.

Origin and Asexual Reproduction of the New Variety

The present variety of apricot tree hereof was discovered by the inventor in his orchard which is located approximately 3½ miles south and ½ mile west of the intersection of David Road and Wheeler Ridge Rd. in Kern County, about 11 miles southwest of Arvin, Calif., in the San Joaquin Valley of central California. The new variety was discovered as a sport of the 'Castlebrite' apricot tree (unpatented). The sport of the new variety was discovered as a limb sport of the 'Castlebrite' apricot tree of one of the scaffold branches thereof. The new variety was asexually reproduced by grafting on June budding on the adjacent land owned by the inventor. The original fruit of this new variety was first observed by the inventor in 1986 and the distinctive characteristics of flavor, later maturity date than the 'Castlebrite' Apricot Tree, and the larger size have been stably reproduced in the asexually reproduced trees.

SUMMARY OF THE NEW VARIETY

The 'Louisa' apricot tree is characterized as to novelty by producing a highly colored, freestone fruit which has much sweeter flavor and milder texture when compared with the fruit of the 'Castlebrite' apricot tree (unpatented) from which it was derived. The fruit of the new variety matures for commercial harvest three days to five days after that of the 'Castlebrite' apricot tree. Fruit produced by the 'Louisa' apricot tree is ripe for commercial harvesting and shipment approximately May 15 to May 25 in the San Joaquin Valley of central California. The new variety of the present invention is most closely similar to the 'Castlebrite' apricot tree, but is distinguishable therefrom by the aforementioned ripening date, by the fact that it is about one to two sizes larger than the fruit of the 'Castlebrite' apricot tree and by the fact that the fruit is substantially sweeter than the fruit of the 'Castlebrite' apricot tree.

BRIEF DESCRIPTION OF THE DRAWING

The accompanying drawing is a color photograph showing mature fruit of the new variety including a first in top plan view showing the stem cavity; a second in bottom plan view showing the apex; a third in side elevation showing the suture thereof; a fourth in side elevation disposed at right angles to the suture plane; and a fifth sectioned along the suture plane and laid open to expose the stone and in the other half, the stone well; one stone of the new variety in side elevation; and representative portions of the foliage and branches, all of the new variety.

DETAILED DESCRIPTION

Referring more specifically to the botanical details of this new and distinct variety of apricot tree, the following has been observed under the ecological conditions prevailing at the orchard of origin which is located at Arvin, Calif. in the San Joaquin Valley of central California. All major color code designations are by reference to the *Dictionary of Color,* by Maerz and Paul, First Edition, 1930. Common color names are also occasionally employed.

Tree

Generally:
*Size.*—Medium.
*Vigor.*—Vigorous and hardy.
*Regularity of bearing.*—Regular for apricots.
Trunk:
*Size.*—Large in diameter.
*Surface texture.*—Moderately coarse, finely furrowed.
*Color.*—Flint (56 C2).
*Lenticels — numbers.*—Numerous.
*Lenticels — size.*—Medium.
Branches:
*Size.*—Average.
*Surface texture — Mature.*—Relatively smooth.
*Surface texture — Immature.*—Smooth.
*Color — one year or older wood.*—Flint (56 C2).
*Color — immature branches.*—Roman green (15-L5).
*Lenticels — numbers.*—Numerous.
*Lenticels — size.*—Medium.

Leaves

Size:
*Generally.*—66 mm (2.64 inches) to 75 mm (3.0 inches).
*Average length.*—75 mm (3.0 inches) to 80 mm (3.2 inches).
*Average width.*—75 mm (3.0 inches) to 80 mm (3.2 inches).
Form: Broadly cordate, leaf tip acuminate.
Color:
*Upwardly disposed surface.*—Mt. Vernon green (23 J8).
*Downwardly disposed surface.*—Cress green (22 K6).
*Leaf vein.*—Canyon (7E6) normally on mid to lower part of leaf.
Marginal form:
*Generally.*—Serrate with the serrations becoming very broad at the basal end of the leaf.
Leaf vein:
*Thickness.*—Medium.
Petiole:
*Length.*—24 mm (0.96 inches) to 29 mm (1.16 inches).
*Thickness.*—Average, 1 mm (0.04 inches).
*Color.*—(7C4) on the underside at the basal portion.
Stem glands:
*Form.*—Globular.
*Position.*—On the petiole.
*Pattern.*—Located alternately on the petiole from 3 mm (0.12 inches) to 4 mm (0.16 inches) to 6 mm (0.24 inches) to 7 mm (0.28 inches) below basal edge of leaf margin.
*Color.*—Mascara (7L8).
Stipules: Two opposite each other with one usually larger than the other. Typically, both are quite small.

Flowers

Pollinization—The new variety is self-pollinating.
Flower buds:
*Size.*—Medium.
*Surface texture.*—Covered with light grey pubescence.
Date of bloom: Feb. 27, 1996.
Size:
*Generally.*—32 mm (1.28 inches) in diameter.
Petals:
*Color.*—White.

Fruit

Maturity when described: Ripe for commercial harvesting and shipment approximately May 15 to May 25 near Arvin in the central San Joaquin Valley of California.
Size:
*Average diameter in the axial plane.*—46 mm (1.84 inches) to 48 mm (1.92 inches).
*Average diameter transverse in the suture plane.*—50 mm (0.2 inches) to 53 mm (2.12 inches).
*Average diameter transverse and at right angles to the suture plane.*—53 mm (2.12 inches) to 55 mm (2.2 inches).
Form:
*Uniformity.*—Medium.
*Symmetry.*—Slightly asymmetrical.
Suture:
*Generally.*—Distinct from base to apex. Suture color is the same as the fruit itself.
Ventral surface:
*Generally.*—Medium in size.
Stem cavity:
*Width.*—25 mm (1.0 inch).
*Depth.*—8 mm (0.32 inches) to 10 mm (0.4 inches).
*Length.*—30 mm (1.2 inches) 35 mm (1.4 inches).
*Shape.*—Slightly oval in form.
Stem:
*Generally.*—Small.
*Caliper.*—5 mm (0.2 inches).
Apex:
*Shape.*—Rounded.
Pistil point:
*Position.*—Apical.
Skin:
*Thickness.*—Average.
*Texture.*—Firm at harvest; becomes soft at maturity.
*Tendency to crack.*—None observed.
*Blush color.*—11 J9.
*Ground color.*—Doubloon Roman Ochre (11 K9).
Flesh:
*Flesh color.*—Near Ponce de Leon (11 J11).
*Surface of pit cavity.*—Same as flesh. Near Ponce de Leon (11 J11).
*Color of pit well.*—Same as flesh. Near Ponce de Leon (11 J11).
*Juice production.*—Fair.
*Flavor.*—Very good, well balanced.
*Aroma.*—Moderate, pleasant.
*Texture.*—Relatively tender.
*Fibers — numbers.*—Few to numerous.
*Fibers — texture.*—Relatively tender.
*Ripening.*—Evenly.
*Eating quality.*—Very good. Sweeter than the fruit of the 'Castlebrite' apricot tree.
Stone:
*Attachment.*—Freestone.
*Fibers — numbers.*—Few.
*Fibers — length.*—Moderately short.
*Size — length.*—25 mm (1.0 inch) to 27 mm (1.08 inches).
*Size — width.*—20 mm (0.8 inches) to 22 mm (0.88 inches).
*Size — thickness.*—10 mm (0.4 inches).
*Form — generally.*—Globose.
*Apex — shape.*—Very smooth and rounded.
*Color — dry.*—Yucatan Cathay — Mexican and French (12 L9).

*Base — shape.*—Generally rounded.

*Sides — Generally.*—Relatively smooth, slightly unequal with slightly pebbled surface, sides equal to slightly unequal.

*Hilum.*—Average. Generally a small or narrow with edge nearly eroded.

*Ridges.*—Two slight raised ridges; one on each side of the main ridge run from the base to the apex and are roughly parallel to, but 4 mm (0.16 inches) to 5 mm (0.2 inches) below, both ridges converge with the ventral edge both basally and apically. Several small pits are usually present along, and on both sides, of the ventral suture area.

*Dorsal edge — shape.*—Rounded with a deep wide groove present apically and basally but not in the mid stone area along the dorsal edge. This mid area of the dorsal edge is quite smooth, with the exception of the presence of several large oval pits.

*Ventral edge.*—Medium thickness with a narrow, slightly raised wing from the base, becoming more reaching to the apex.

*Tendency to split.*—None observed.

Use: Fresh market apricot for use in local markets, as well as for long distance shipping.

Keeping quality: Good.

Resistance to disease: Unknown.

Harvesting: Normal for apricots.

Shipping and handling qualities: Good.

Although the new variety of apricot tree possesses the described characteristics noted above as a result of the growing conditions prevailing near Arvin, Calif. in the central part of the San Joaquin Valley of central California, it is to be understood that variations of the usual magnitude and characteristics incident to changes in growing conditions, irrigation, fertilization, pruning, pest control, climatic variation and the like are to be expected.

Having thus described and illustrated my new variety of apricot tree, what I claim as new and desire to be secured by Plant Letters Patent is:

1. A new and distinct variety of apricot tree substantially as illustrated and described which is somewhat remotely similar to the 'Castlebrite' apricot tree (unpatented) from which it was derived, but from which it is distinguished by producing fruit which are mature for commercial harvesting and shipment approximately May 15 to May 25, or about three days to five days after the 'Castlebrite' apricot tree, in the San Joaquin Valley of central California and which produces larger freestone fruit with a substantially sweeter flavor and milder texture.

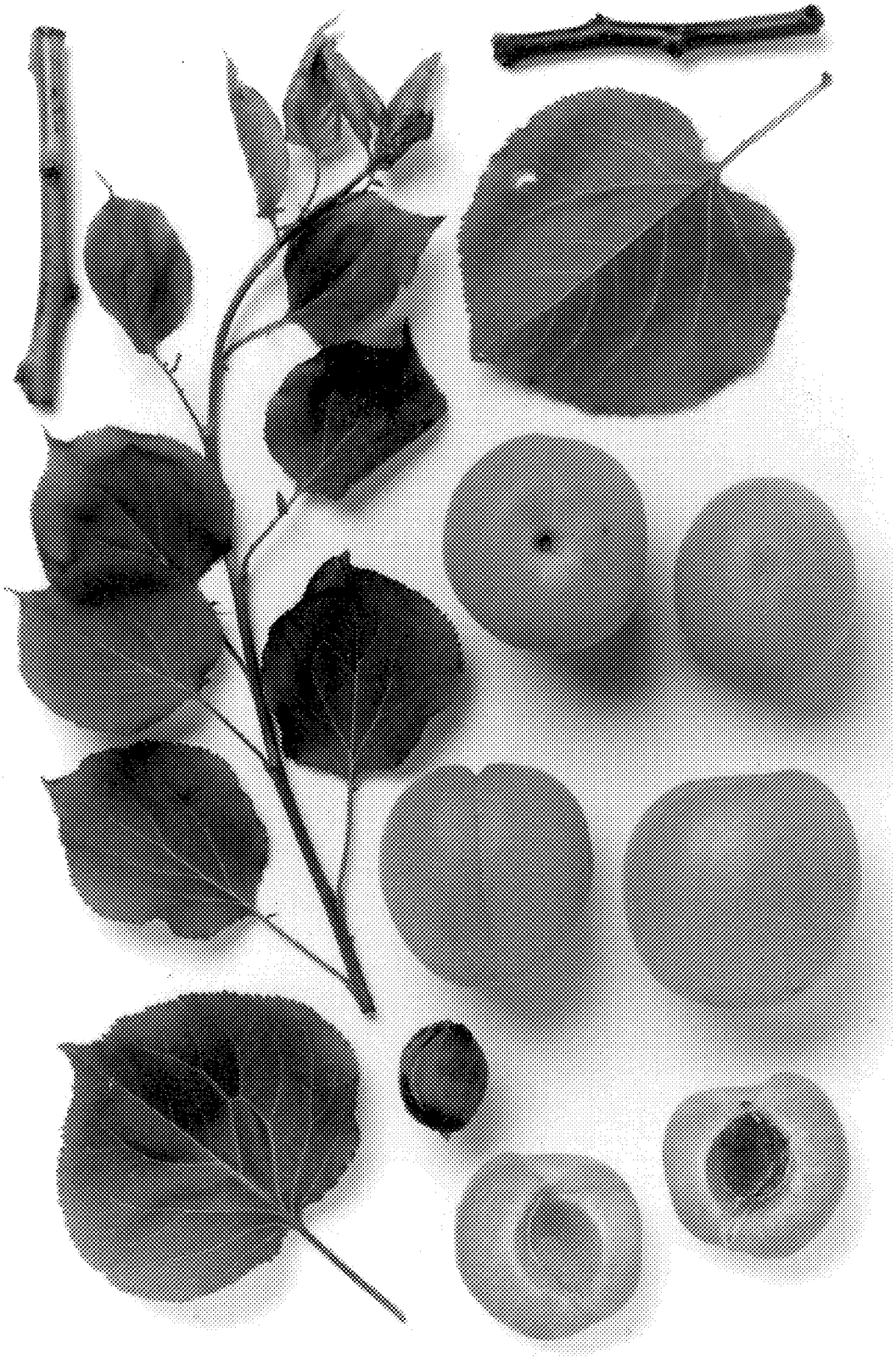

* * * * *